(12) United States Patent
León Monzón et al.

(10) Patent No.: US 9,206,243 B2
(45) Date of Patent: Dec. 8, 2015

(54) IL-2 DERIVATIVE POLYPEPTIDES

(75) Inventors: Kalet León Monzón, Havana (CU); Tania Carmenate Portilla, Havana (CU); Saumel Pérez Rodriguez, Artemisa (CU); Neris Michel Enamorado Escalona, Havana (CU); Agustin Bienvenido Lage Dávila, Havana (CU)

(73) Assignee: CENTRO DE IMMUNOLOGIA MOLECULAR, Havana (CU)

( * ) Notice: Subject to any disclaimer, the term of this patent is extended or adjusted under 35 U.S.C. 154(b) by 44 days.

(21) Appl. No.: 13/885,021

(22) PCT Filed: Nov. 10, 2011

(86) PCT No.: PCT/CU2011/000007
§ 371 (c)(1),
(2), (4) Date: Jun. 6, 2013

(87) PCT Pub. No.: WO2012/062228
PCT Pub. Date: May 18, 2012

(65) Prior Publication Data
US 2014/0314709 A1 Oct. 23, 2014

(30) Foreign Application Priority Data

Nov. 12, 2010 (CU) .................................. P/2010/216

(51) Int. Cl.
| | | |
|---|---|---|
| *C07K 14/55* | (2006.01) | |
| *A61K 38/00* | (2006.01) | |
| *A61K 39/00* | (2006.01) | |
| *A61K 47/48* | (2006.01) | |
| *A61K 38/20* | (2006.01) | |
| *C07K 14/76* | (2006.01) | |

(52) U.S. Cl.
CPC ............ *C07K 14/55* (2013.01); *A61K 38/2013* (2013.01); *A61K 47/48423* (2013.01); *C07K 14/76* (2013.01); *A61K 38/00* (2013.01); *A61K 2039/55533* (2013.01); *C07K 2319/33* (2013.01)

(58) Field of Classification Search
CPC ............... C07K 14/55; A61K 38/2013; A61K 2039/55533; A61K 47/48423
See application file for complete search history.

(56) References Cited

U.S. PATENT DOCUMENTS

| | | | |
|---|---|---|---|
| 4,853,332 | A | 8/1989 | Mark et al. |
| 4,959,314 | A | 9/1990 | Mark et al. |
| 5,116,943 | A | 5/1992 | Koths et al. |
| 5,229,109 | A | 7/1993 | Grimm et al. |
| 6,955,807 | B1 | 10/2005 | Shanafelt et al. |
| 7,105,653 | B2 | 9/2006 | Shanafelt et al. |
| 7,186,804 | B2 | 3/2007 | Gillies et al. |
| 2005/0142106 | A1 | 6/2005 | Wittrup et al. |

FOREIGN PATENT DOCUMENTS

WO WO2008/003473 * 1/2008

OTHER PUBLICATIONS

Ahmadzadeh, M., et al., "IL-2 administration increases CD4+CD25hiFoxp3+ 6regulatory T cells in cancer patients", (2006) Blood. 107, 2409-14.
Almeida, A.R., et al. Homeostasis of Peripheral CD4+ T Cells: IL-2R α and IL-2 Shape a Population of Regulatory Cells That Control CD4 + T Cell Numbers, (2002) J Immunol. 169, 4850-60.
Blattman, J.N., et al. "Therapeutic use of IL-2 to enhance antiviral T-cell responses in vivo", (2003) Nat Med. 9, 540-7.
Boyman, O., Kovar, et al., "Selective Stimulation of T Cell Subsets with Antibody-Cytokin Immune Complexes", (2006) Science. 311, 1924-1927.
Boyman, O., et al. "Potential use of IL-2/anti-IL-2 antibody immune complexes for the treatment of cancer and autoimmune disease", (2006) Expert Opin Biol Ther. 6, 1323-31.
Fishman, M., et al. "Phase II Trial of B7-1 (CD-86) Transduced, Cultured Autologous Tumor Cell Vaccine Plus Subcutaneous Interleukin-2 for Treatment of Stage IV Renal Cell Carcinoma", (2008) J Immunother. 31, 72-80.
Kamimura, D., et al. "IL-2 in Vivo Activities and Antitumor Efficacy Enhanced by an Anti-IL-2 mAB", (2006) J Immunol. 177, 306-14.
Kreitman, R.J., "Recombinant Immunotoxins Containing Truncated Bacterial Toxins for the Treatment of Hematologic Malignancies", (2009) BioDrugs, 2009; 23(1):1-13.
Kuniyasu, Y., et al. "Naturally anergic and suppressive CD25+CD4+T cells as a functionally and phenotypically distinct immunoregulatory T cell subpopulation"(2000) Int Immunol. 12, 1145-55.
Lin, C.T., et al. "DNA vaccines encoding IL-2 linked to HPV-16 E7 antigen generate enahnced E7-specific CTL responses and antitumor activity", (2007) Immunol Lett. 114, 86-93.

(Continued)

*Primary Examiner* — Robert Landsman
*Assistant Examiner* — Bruce D Hissong
(74) *Attorney, Agent, or Firm* — Rothwell, Figg, Ernst & Manbeck, P.C.

(57) ABSTRACT

The present invention relates to polypeptides which share primary sequence with human IL-2, except for several amino acids that have been mutated. The mutations introduced substantially reduce the ability of these polypeptides to stimulate in vitro and in vivo regulatory T cells (T CD4+CD25+ FoxP3+) and make them more effective in the therapy of murine transplantable tumors. Also includes therapeutic uses of these mutated variants, used alone or in combination with vaccines for the therapy of diseases such as cancer or infections where the activity of regulatory T cells (Tregs) is relevant. In another aspect the present invention relates to pharmaceutical compositions comprising as active principle the polypeptides disclosed. Finally, the present invention relates to the therapeutic use of the polypeptides and pharmaceutical compositions disclosed due to their modulating effect of the immune system on diseases like cancer and chronic infectious diseases.

33 Claims, 6 Drawing Sheets

(56) References Cited

OTHER PUBLICATIONS

Litzinger, M.T., et al., "IL-2 immunotoxin denileukin diftitox reduces regulatory T cells and enhances vaccine-mediated T-cell immunity" (2007) Blood. 110, 3192-201.

Malek, T.R., et al. "Tolerance, Not Immunity, Crucially Depends on IL-2", (2004) Nat Rev Immunol. 4, 665-74.

Morse, M.A.,et al., "Depletion of human regulatory T Cells specifically enhances antigen-specific immune responsese to cancer vaccines", (2008) Blood. 112, 610-8.

Murakami, M., "CD25+CD4+ T cells contribute to the control of memory CD8+ T cells", (2002) Proc Natl Acad Sci USA. 99, 8832-7.

Onizuka, S., et al., "Tumor Rejection by in Vivo Administration of Anti-CD25 (Interleukin-2 Receptor α) Monoclonal Antibody", (1999) Cancer Res. 59, 3128-33.

Pandiyan, P., et al., "CD4+CD25+Foxp3+ regulatory T cells induced cytokine deprivation-mediated apoptosis of effector CD4+ T cells", (2007) Nat Immunol. 8, 1353-62.

Quezada, S.A., "CTLA4 blockade and GM-CSF combination immunotherapy alters the intratumor balance of effector and regulatory T cells", (2006) J Clin Invest. 116, 1935-45.

de la Rosa, M., et al., Interleukin-2 is essential for CD4+CD25+ regulatory T cell function, (2004) Eur J Immunol. 34, 2480-8.

Kudo-Saito, C., et al., Intratumoral delivery of vector mediated IL-2 in combination with vaccine results in enhanced T cell adidity and anti-tumor activity, (2007) Cancer Immunol Immunother. 56, 1897-910.

Smith, K.A. "Interleukin-2: Inception, Impact, and Implications", (1988) Science. 240, 1169-76.

Takahashi, T. et al. "Immunologic self-tolerance maintained by CD25+CD4+ naturally anergic and suppressive T cells" induction of autoimmune disease by breaking their anergic/suppressive state, (1998) Int Immunol. 10, 1969-80.

Thornton, A.M., et al. "CD4+CD25+ Immunoregulatory T Cells Suppress Polyclonal T Cell Activation In Vitro by Inhibiting Interleukin 2 Production", (1998) J Exp Med. 188, 287-96.

Tomala, J., "In Vivo Expansion of Activated Naive CD8+ T Cells and NK Cells Driven by Complexes of IL-2 and Anti-IL-2 Monoclonal Antibody as Novel Approach of Cancer Immunotherapy",. (2009) J Immunol. 183, 4904-4912.

Wolf, M., et al. "Control of T cell hyperactivation in IL-2-deficient mice by CD4+CD25+ and CD4+CD25+Tcells: evidence for two distinct regulatory mechanisms", (2001) Eur J Immunol. 31, 1637-45.

\* cited by examiner a

Anti 6His-PE b a b a b

IL-2 DERIVATIVE POLYPEPTIDES

CROSS REFERENCE TO RELATED APPLICATION

This application is a 35 U.S.C. 371 National Phase Entry Application from PCT/CU2011/000007, filed Nov. 10, 2011, which claims the benefit of Cuban Patent Application No. P/2010/216 filed on Nov. 12, 2010 the disclosure of which is incorporated herein in its entirety by reference.

SCOPE OF THE INVENTION

The present invention relates to immunology. It relates specifically to the therapeutic modulation of the immune system by means of natural molecule analogues that have the agonistic action of the original molecule but, unexpectedly, showed a superior therapeutic efficacy.

BACKGROUND OF THE INVENTION

Interleukin 2 (IL-2) was first growth factor described for T cells. Since its discovery it was observed its ability to promote proliferation and survival of T in vitro cells (Smith, K A. (1988) Science. 240, 1169-76), as well as to boost immune response in the context of T viral infections (Blattman, J N, et al. (2003) Nat Med 9, 540-7) or vaccines (Fishman, M., et al. (2008) J Immunother. 31, 72-80, Kudo-Saito, C., et al. (2007) Cancer Immunol Immunother. 56, 1897-910; Lin, C T., et al. (2007) Immunol Lett. 114, 86-93). However, this classical role of IL-2 as a promoter of T immune response has been questioned recently by numerous experimental data (Almeida, A R., et al. (2002) J Immunol. 169, 4850-60; de la Rosa, M., et al. (2004) Eur J Immunol. 34, 2480-8, Malek; T R, et al. (2004) Nat Rev Immunol. 4, 665-74) showing that this cytokine is an homeostatic growth factor for natural regulatory T cells CD4+CD25+FoxP3+ (Tregs). Interleukin-2 has also been proposed as a major player in the mechanism by which regulatory T cells suppress the activity and expansion of other effector cells such as CD4 T helper cells, cytotoxic CD8 T cells and natural killer (NK) cells. In particular it has been recently proposed that regulatory T cells suppress other T cells, inducing the local decrease in the levels of IL-2 (Pandiyan, P., et al. (2007) Nat Immunol. 8, 1353-1362). This suppressive effect is based on: a) their ability to directly inhibit that effector T cells produce new IL-2 (Almeida, A R., et al. (2002) J Immunol. 169, 4850-60; Takahashi, T., et al. (1998) Int Immunol. 10, 1969-80; Thornton, A M., et al. (1998) J Exp Med 188, 287-96; Wolf, M., et al. (2001) Eur J Immunol. 31, 1637-45); b) their ability to sequester, internalize and degrade quickly the IL-2 present in their microenvironment (Pandiyan, P., et al. (2007) Nat Immunol. 8, 1353-62) and c) its ability to over-express the alpha chain of the IL-2 receptor (Kuniyasu, Y., et al. (2000) Int Immunol. 12, 1145-1155), which allows for a more efficient use of IL-2 when its concentrations are low.

In summary, IL-2 is a highly pleiotropic cytokine which is very relevant in the biological activity of different cell populations. This property makes the IL-2 an important node in the regulation of the immune response, making it an attractive target for therapies and complex immune modulation.

IL-2 has been used for several years in cancer therapy. In particular its use at high doses is an approved therapy in several countries for the treatment of metastatic melanoma and renal cell carcinoma. However, the direct use of IL-2 in patients is severely limited by its toxic effects and low efficacy. So much so that only 20% of eligible patients receive IL-2 based therapy and only 17% of those patients treated show an objective response. A likely explanation for this dramatic failure in the clinic setting is that therapy with native IL-2 also stimulates populations of regulatory T cells (Ahmadzadeh, M., et al. (2006) Blood. 107, 2409-14) which dampen the desired immuno-stimulation. Nowadays large amounts of pre-clinical evidence support this idea. In particular, experiments in murine models show that the primary activity of the IL-2 injected in vivo is the homeostatic expansion of natural regulatory T cells. Several strategies have been developed to mitigate the toxic effects of IL-2 therapy. Some of these strategies are based on the use of mutated variants of IL-2, designed to increase the capacity of this molecule to signal mainly by the high affinity receptor (alpha, beta and gamma chains) and not by the intermediate affinity receptor (beta and gamma chains). The basic idea is to promote signaling in T cells instead of signaling in NK cells, which are believed to be responsible for the observed toxic effects. The following inventions are in this line of work: U.S. Pat. No. 7,186,804, U.S. Pat. No. 7,105,653, U.S. Pat. No. 6,955,807, U.S. Pat. No. 5,229,109, U.S. Patent Application 20050142106. It is important to note that none of these inventions relates to muteins of IL-2 that have greater therapeutic efficacy than the in vivo native IL-2, based on their decreased ability to stimulate natural regulatory T cells.

Other mutated variants of IL-2 have been created with the aim of increasing their pharmacological activity by, for example, improving its folding or increasing their lifetime in blood. Among others, the following inventions are in this line of work: U.S. Pat. No. 4,959,314, U.S. Pat. No. 5,116,943, U.S. Pat. No. 4,853,332. Again, none of these muteins have a decreased ability to activate regulatory T cells or shows greater therapeutic efficacy.

Finally, it should be mentioned that in the literature there are numerous proposals of therapeutic agents (Kreitman, R. J. (2009) Curr Pharm Des. 15, 2652-64; Litzinger, M. T., Fernando, R., Curiel, T. J., Grosenbach, D. W., Schlom, J. and Palena, C. (2007) Blood. 110, 3192-201; Morse, M. A., Hobeika, A. C., Osada, T., Serra, D., Niedzwiecki, D., Lyerly, H. K. and Clay, T. M. (2008) Blood. 112, 610-8; Onizuka, S., Tawara, I., Shimizu, J., Sakaguchi, S., Fujita, T. and Nakayama, E. (1999) Cancer Res. 59, 3128-33; Quezada, S. A., Peggs, K. S., Curran, M. A. and Allison, J. P. (2006) J Clin Invest. 116, 1935-45) that propose to modulate or reduce the activity of regulatory cells vivo. These therapeutic agents have been tested in animal models or even in patients as a direct therapy of cancer or to enhance the effect of vaccines. There are also some reports that propose to modulate the activity of IL-2, in particular monoclonal antibodies (Boyman, O., Kovar, M., Rubinstein, M. P., Surh, C. D. and Sprent, J. (2006) Science. 311, 1924-1927; Boyman, O., et al. (2006) Expert Opin Biol Ther. 6, 1323-31; Kamimura, D., et al. (2006) J Immunol. 177, 306-14; Murakami, M., Sakamoto, A., Bender, J., Kappler, J. and Marrack, P. (2002) Proc Natl Acad Sci USA. 99, 8832-7; Tomala, J., Chmelova, H., Mrkvan, T., Rihova, B. and Kovar, M. (2009) J Immunol. 183, 4904-4912), to promote better or more effective immune responses. However, to our knowledge, there is no report in the literature, based on mutated variants of IL-2, showing the possibility of obtaining greater therapeutic efficacy based on their decreased ability to stimulate natural regulatory T cells.

BRIEF DESCRIPTION OF THE INVENTION

The present invention relates to the production of mutated variants of IL-2, which show greater therapeutic efficacy than the native IL-2 in transplantable murine tumor models. These muteins are characterized by being partial agonists of IL-2 activity and selected due to their particularly low ability to stimulate natural regulatory T cells (T CD4+CD25+FoxP3+) in vitro and/or in vivo. The in vivo therapeutic efficacy of these muteins offers a practical solution to improve IL-2 therapy in malignant tumors. In particular, these muteins will provide a way to overcome the limitations observed in native IL-2 therapy which are derived from their proven ability to expand in vivo natural regulatory T cells. The present invention relates to polypeptides which share their primary sequence with the human IL-2, except for several amino acids that have been mutated. The mutations introduced substantially reduce the ability of these polypeptides to stimulate in vitro and in vivo regulatory T cells (T CD4+CD25+FoxP3+) and give IL-2 a greater efficacy in the therapy of murine transplantable tumors. The present invention also includes therapeutic uses of these mutated variants, alone or in combination with vaccines for therapy of diseases such as cancer or infections where the activity of regulatory T cells (Tregs) is relevant.

The present invention allows for a substantial improvement of the current strategies of immunomodulation based on IL-2, both for in the direct therapy of cancer and in combination with different vaccines. In particular the replacement of the native IL-2 by the mutated variants described herein, will prevent the expansion of regulatory T cells which markedly reduce the desired therapeutic effects.

DETAILED DESCRIPTION OF THE INVENTION

Obtainment of IL-2 Analogue Polypeptides

The present invention relates to polypeptides of 100 to 500 amino acids in length, preferably of 140 residues size whose apparent molecular weight is at least 15 kD. These polypeptides maintain high sequence identity, more than 90%, with native IL-2. In a region of their sequence, they include 3 to 6 mutations as compared to the native IL-2. In these positions, these polypeptides are mutated introducing amino acid residues different from those in the same position in the native IL-2. The aminoacids that replace the original residues are selected to have physicochemical properties quite different to the ones of the original amino acid, changing the polar residue for nonpolar, uncharged for charged, large for small, acid for base, among others changes.

The polypeptides of the present invention may be referred to as immunomodulatory polypeptides, IL-2 analogs or IL-2 muteins, among others names. These polypeptides are designed based on the 3D structure of the IL-2 receptor complex (available in PDB public database), introducing mutations mainly in the positions of the IL-2 corresponding to amino acids significantly exposed to the solvent and that are highly conserved in the IL-2 from different species (sequences obtained from Swissprot database). The amino acids exposed to the solvent of the type mentioned above are identified using bioinformatics softwares for visualization of protein structures such as RASMOL, SwissPDBviewer or others. The conserved positions in the sequence of IL-2 were identified using bioinformatics softwares for multiple sequence alignment, e.g., Fasta, ClusterW or others.

The polypeptides of this invention can be obtained by various strategies, including by protein synthesis. They could also be obtained by genetic engineering techniques, for instance by expressing them in bacteria such as *E. coli* or other bacteria and also in mammalian cells such as NSO cells or other mammalian cells. Point mutations at specific positions may also be obtained by site-directed mutagenesis techniques by means of polymerase chain reaction assay (PCR).

Unexpectedly, the inventors found a substantial advantage of these muteins with respect to the traditional use of native IL-2. This advantage lies in their increased effectiveness in tumor therapy, derived from its ability to prevent the expansion of regulatory T cells.

Selection of the polypeptide analogs of IL-2 in terms of biological activity;

The polypeptides of the present invention are selected by the following properties:

1) Agonist action of native IL-2. This property can be evaluated directly in in-vitro proliferation assays with cell lines dependent on IL-2 such as CTLL2 or Kitt225, or with assays with mixtures of murine and/or human T lymphocytes. These muteins must have a specific stimulatory activity 5 to 50 times less than that of native IL-2 in these trials.

2) Loss of capacity, as compared to native IL-2, to stimulate in vitro and/or in vivo populations of regulatory T cells. This property can be assessed, for instance, by studying the ability of the muteins of the present invention, as compared to those of native IL-2, to directly induce expansion of T CD4+CD25+cells, purified from naïve mice and stimulated with an in vitro anti-CD3 antibody. It can be also assessed by injecting, intraperitoneally or subcutaneously, these muteins or the native IL-2 in mice, for five days, and evaluating its effect on the expansion or increase in the rate of proliferation of populations of regulatory T cells (TCD4+CD25+FoxP3+). The activity of the mutated IL-2 on Treg cells must be at least 1000 times lower than that of native IL-2 in these trials.

3) Increased therapeutic effect with respect to the native IL2 in animal models. This property can be assessed, for example, by comparing the antitumor or anti-metastatic effect of the muteins and the native IL-2 as monotherapy in transplantable tumor models (e.g. B16 melanoma). It can also be evaluated through the potentiating effect of the cellular and/or humoral response to a vaccine of interest. The muteins must show greater therapeutic efficacy than the native IL-2 in doses containing an equal total mass of proteins of IL-2 and the mutein.

The present invention is particularly related to the muteins specified on Table 1. These muteins have multiple aminoacids substitutions which give them the above-mentioned properties.

TABLE 1

Designed Muteins that have the three basic properties described in this patent. The mutations are referred to according to the numbering of the human IL-2.

| Mutations |
| --- |
| R38K, F42I, Y45N, E62L, E68V |
| R38K, F42Q, Y45E, E68V |
| R38A, F42I, Y45N, E62L, E68V |
| R38K, F42K, Y45R, E62L, E68V |
| R38K, F42I, Y45E, E68V |
| R38A, F42A, Y45A, E62A |

The present invention also includes additional modifications to the class of IL-2 muteins mentioned above and especially to those described in Table 1. Whether it is to increase their affinity to specific components of the IL-2 receptor, but without affecting or even improving its agonist character that does not stimulate regulatory T cells, or to improve their in vivo pharmacodynamics: increase half-life or reduce their internalization by T cells. These additional mutations may be obtained by rational design with bioinformatics tools, or by using combinatorial molecular libraries of different nature (phage libraries, libraries of gene expression in yeast or bacteria). In another aspect the present invention relates to a fusion protein comprising any of the immunomodulatory polypeptides described above, coupled to a carrier protein. The carrier protein can be Albumin or the Fc region of human immunoglobulins.

Therapeutic Application of IL-2 Analog Polypeptides

This invention also includes pharmaceutical compositions comprising as active ingredient the muteins of IL-2 and its analogs, disclosed by means of the present invention and its potential therapeutic applications in order to enhance the natural or vaccine-induced immune response in diseases such as cancer or chronic infections where regulatory T cells are particularly relevant.

For its therapeutic use, the polypeptide of the present invention should be administered to a subject carrier of the disease independently or in combination with other polypeptides or other substances that facilitate or enhance its therapeutic action. The route of administration may be any route of administration described by the state of the art for parenteral administration of drugs. Preferably it should be administered intravenously, intramuscularly, subcutaneously or intratumorally.

The polypeptides described herein may also be administered as part of a pharmaceutical composition that is used in the treatment of cancer and chronic infectious diseases or to enhance the cellular and/or humoral response to vaccines, as replacement of the native IL2. The polypeptides of the present invention can be used in combination with therapeutic vaccines for cancer or with prophylactic vaccines in infectious diseases where regulatory T cells are relevant.

To obtain the desired therapeutic effect, the polypeptide of the present invention should be administered at doses high enough to ensure its concentration in the peripheral lymph node or in the peripheral site relevant to the disease under study and within the range of concentrations in which the mutein which shows an immune-stimulatory effect. The dose in question should therefore be adjusted according to the type of disease and the route of administration under study. For example in the case of tumor therapy, the dose should be adjusted to achieve concentrations of the mutein inside the tumor and/or in the loco-regional lymph node so as to ensure the stimulation of an antitumor immune response. The dose ranges to explore can range from hundreds of micrograms to hundreds of milligrams per dose. For applications in which the mutein replaces traditional therapy with native IL-2 the mutein dose used should be less than or equivalent in activity (determined using assay with CTLL2 line) to the one traditionally used for native IL-2.

The number of administrations to apply should also be adjusted according to the biodistribution of the mutein in question. In general, the aforementioned effective levels should be maintained for 2 to 30 consecutive days. It should be noted, for example, that if the mutein is coupled to a carrier protein, the frequency of its administration shall be adjusted accordingly. For applications in which the native IL-2 is replaced the scheme of administration of the mutein may be similar to that used in traditional therapy.

Therapeutic action should be understood by, full or partial remission of the symptoms of the disease. In cancer, a decrease in tumor volume or an increase in the time before relapse will be, among others, the criterion of remission of the disease.

The polypeptides of the invention are particularly useful in the therapy of tumors such as melanomas and renal tumors.

EXAMPLES

Example 1

Design of the IL-2 Muteins

Figure 1:
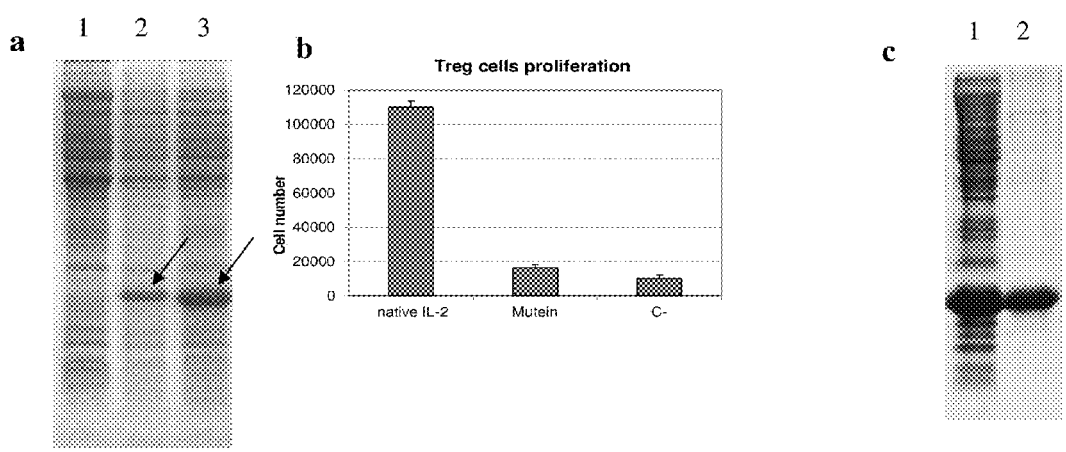
FIG. 1. Obtainment of the mutein. a) Expression of the mutein in strain BL21 DE3 of *E. coli* evaluated by electrophoresis in SDS-polyacrylamide gel (SDS-PAGE), lane 1: Total proteins of BL21DE3 strain, negative control of expression; lanes 2 and 3: Two examples of the expression levels achieved in this strain, the arrow indicates the band corresponding to the mutein. b) Reverse phase chromatogram showing the main final purification step of the protein, the arrow indicates the peak corresponding to the protein of interest. c) Purification of the mutein assessed by SDS-PAGE 1: Results of the process of inclusion body isolation, 2: mutein obtained after purification by reverse phase FIG. 2. Assessment of the agonist character of IL-2 mutein. a) Measurement by flow cytometry of the binding ability of the mutein to the surface of the CTLL2 cell line. Both IL-2 and mutein were detected using an anti 6His tag MAb b) The graph shows the ability of the mutein to induce the proliferation of the IL-2-dependent T-cell line CTLL2, compared with native IL-2. The proliferation was measured by MTT incorporation.

The muteins were designed computationally, from bioinformatics techniques, using as basis the reported structure of human IL-2 in database PDB (Protein Data Bank) and the amino acid sequences of IL-2 in various species that are available in Swissprot database. Several muteins were designed including 3 to 6 mutations (introducing non-conservative amino acid substitutions) in solvent-exposed and highly conserved residues. These muteins were expressed in E. coli from a plasmid construction in pET28a vector including a target sequence of 6 histidines at the amino terminal. The muteins were purified by reverse phase (FIG. 1) and a high purity (>95%) was obtained. The muteins obtained were selected from their properties in experimental assays both in vitro and in vivo, to show the 3 basic properties described in the body of this invention. Out of all the muteins constructed Table 1 describes a set of specific mutations that have the desired property of being agonists of the activity of IL-2 without appreciably stimulating regulatory T cells and which show greater therapeutic efficacy than native IL-2 in the treatment of transplantable murine tumors. Table 2 shows the others muteins constructed that did not show the desired properties.

TABLE 2

Muteins constructed that do not have the basic properties described in this patent. The mutations are referred to according the numbering of the human IL-2.

Mutations

Q22V, Q126A, I129D, S130G
L18N, Q126Y, S130R
Q13Y, Q126Y, I129D, S130R
L18N, Q22V, T123A, I129D, S130R
R38A, F42A, Q126Y, I129D
Q126Y, I129D, E62L, E68V

Example 2

Demonstration of the Agonist Nature of the IL-2 Muteins Designed

Figure 2:
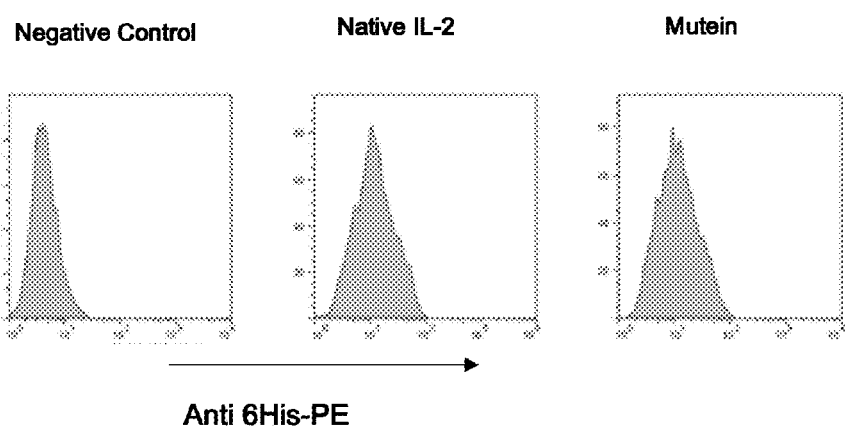
Figure 2:
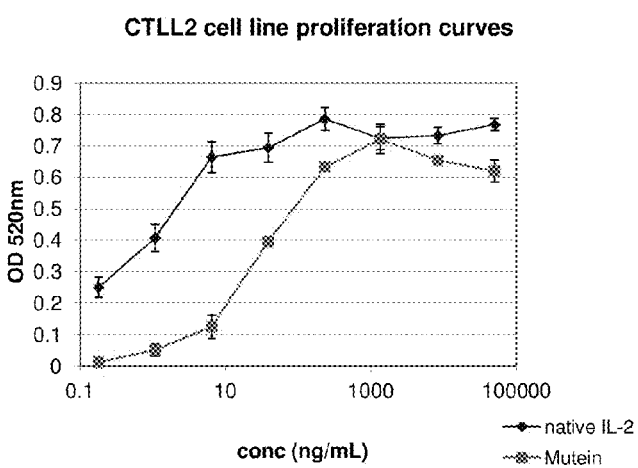

FIG. 2 illustrates how the muteins mentioned in Table 1 bind to the components of the IL-2 receptor on the surface of CTLL2 cell line (FIG. 2a). The constructed muteins bind to the CTLL2 cells, which are known to have on their surface both high affinity and intermediate affinity receptors for IL-2. The binding detected in our assays appears to be similar to that obtained with native IL-2. FIG. 2b illustrates the capacity of the muteins shown in Table 1 to stimulate the growth of CTLL2 cell line (FIG. 2b). These muteins behave as partial agonists of the activity of IL-2 in this assay. Their specific activity is between 5 and 50 times lower than that of native IL-2.

Example 3

Effect of IL-2 Muteins on Regulatory T Cells

Figure 3:
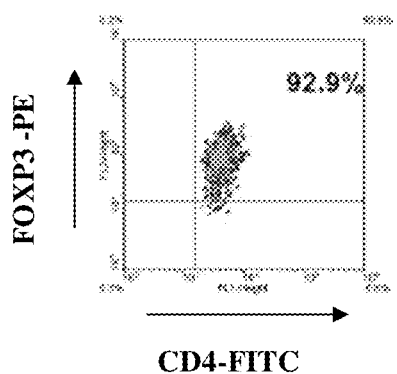
FIG. 3. The mutein does not induce in vitro proliferation of regulatory T cells. a) Flow cytometry graph showing the purity of CD3+CD4+CD25+ population purified from C57BL/6 mouse lymphonodes. b) Treg cells were stimulated in vitro with anti-CD3 mAb and native IL-2 was administered to them at a concentration of 0.5 ng/mL or mutein at a concentration of 32 ng/mL for 72 hours, the graph shows the number of live cells recovered after each treatment compared with the control where no cytokine was added. The selected concentrations correspond to the concentration at which each molecule induces the same proliferation of CTLL2 line.
Figure 3:
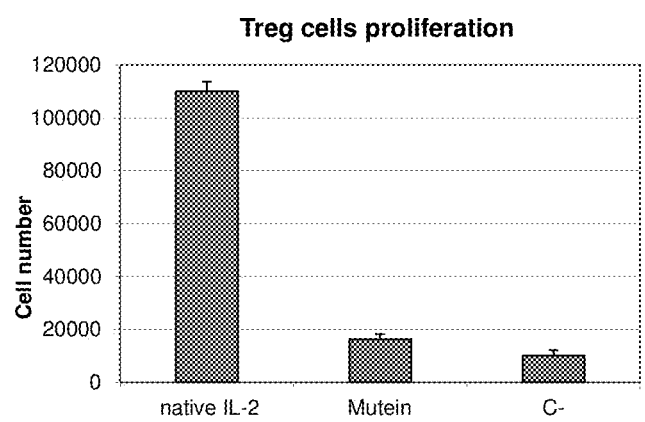

The muteins described in Table 1 show a very low capacity to stimulate regulatory T cells in vitro (FIG. 3). As shown in this figure, while the native IL-2 is able to induce strong proliferation of regulatory T cells (T CD4+CD25+FoxP3+) stimulated with plate-bound anti-CD3 antibody. The muteins described in Table 1 in mass concentrations significantly higher than that of the native IL-2 did not stimulate the regulatory T cells. It must be added that the results described above are valid even if the amount of mutein to use is increased so as to use an amount equivalent in activity to the native IL-2 in the proliferation assay with CTLL2 line. The muteins described in Table 1 typically exhibit a capacity to stimulate regulatory T cells at least 1000 times lower than that of native IL-2

Example 4

Figure 4:
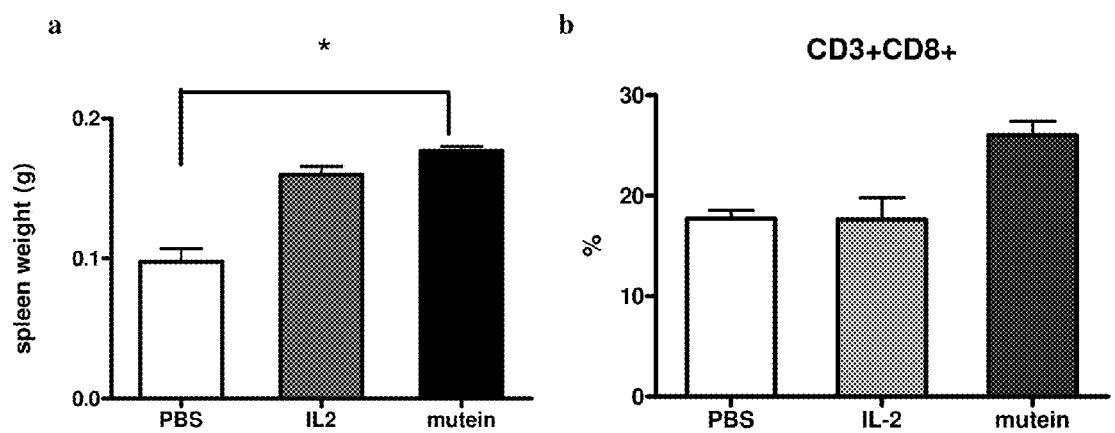
FIG. 4. Evaluation of the effect of treatment with mutein on the proliferation of cell populations. a) Quantification of the relative weights of the spleens of mice treated with the mutein for five days. The weights of the spleens of treated mice were statistically higher than those of the control group. Kruskal-Wallis nonparametric test and Dunn multiple comparison. b) Measurement of the population of T CD8+cells, the graph shows the percentages of this population.

Characterization of the In Vivo Immunostimulatory Activity of the Muteins Designed The muteins described in Table 1 show an increased in vivo immunostimulatory capacity. FIGS. 4a, b show how the muteins induce a splenomegaly greater than that of the native IL2 in naive mice, after treatment for five days with two daily doses of 20 μg of the mutein administered intraperitoneally. This stimulation correlates with a clear increase of effector populations, like T CD8+ lymphocytes. As relevant observation we can state that treatment with these muteins does not stimulate expansion of regulatory T cells (T CD4+CD25+ FoxP3+) in contrast to what was observed in the case of the native IL2 (FIG. 4c, d).

Example 5

Figure 5:
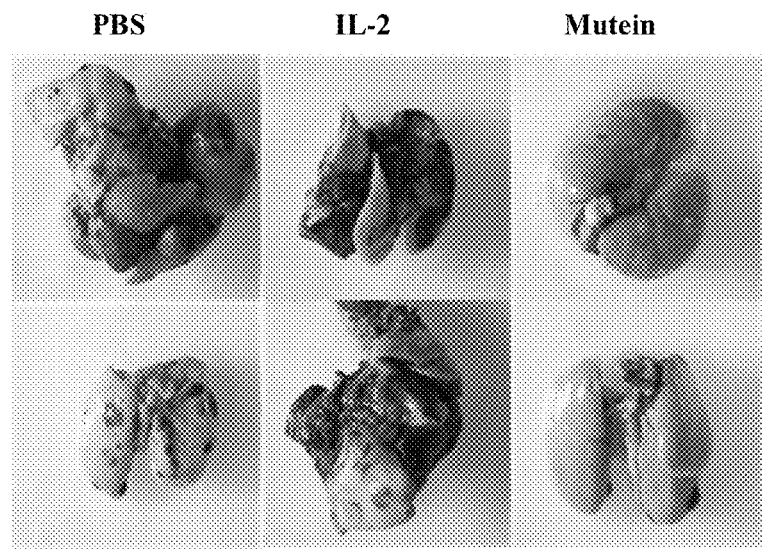
FIG. 5. The mutein is more efficient than native IL-2 in the reduction of metastases in the experimental metastasis model of melanoma MB16F0 line. a) Representative photographs of lungs for each treatment. b) Quantification of pulmonary metastases in each group.
Figure 5:
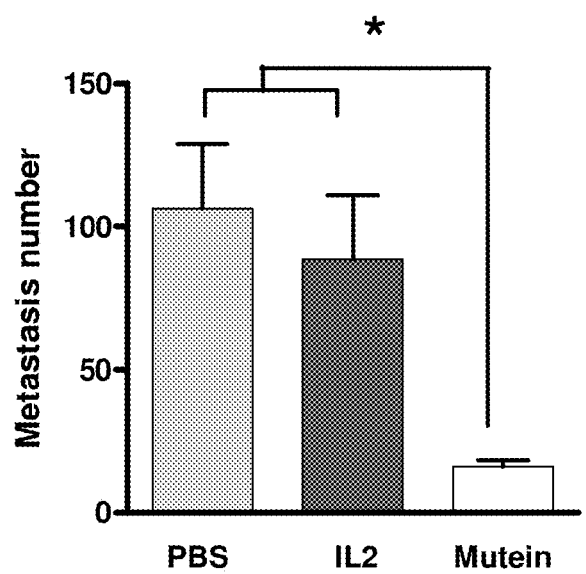

Measuring the Therapeutic Efficacy of the Muteins in a Murine Model of Transplantable Tumors The increase in the therapeutic efficacy of the muteins designed in a murine model of transplantable tumors was proven. The muteins described in Table 1 show an increased efficacy for the treatment of lung metastases in a MB16 murine melanoma model. FIG. 5 shows how treatment for 5 days with two daily doses of 20 μg of the muteins in Table 1 administered intraperitoneally has a strong antimetastatic effect, which is not observed in the groups treated with equal doses of native IL-2.

Example 6

Measurement of Mutein Capacity for Potentiating the Antitumor Vaccine Effect

Figure 6:
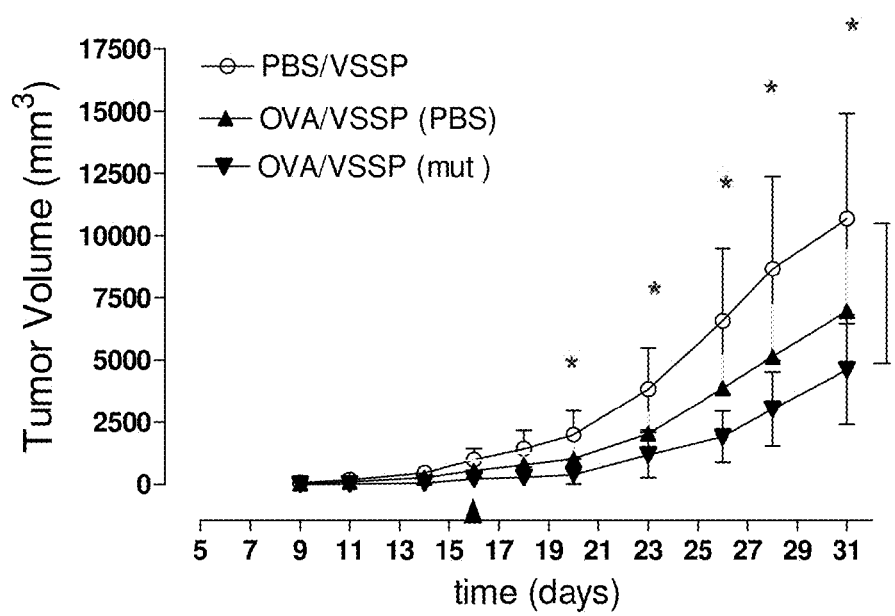
FIG. 6. The treatment with the combination of the mutein and the OVA/VSSP vaccine potentiate the antitumor effect of the vaccine. The tumor-bearing mice were treated with the OVA/VSSP vaccine alone or in combination with the mutein. The graph shows the tumor growth curves, the group treated with the combination showed greater tumor growth reduction, being statistically different form the control group.

The capacity of designed mutein, for potentiating the antitumor vaccine effect was proven. It was used a primary tumor model with the EG7 cell line, a tumor cell line genetically modified for expressing OVA antigen. The tumor-bearing mice were immunized with OVA antigen adjuvanted with VSSP alone, or in combination with the mutein. FIG. 6 shows that the reduction of tumor growth was greater for mice treated with the combination, than for mice treated with the vaccine alone.

The invention claimed is:

1. An agonist polypeptide of IL-2, characterized by 95% homology with the sequence of native wild-type human IL-2 and wherein said polypeptide is at least 1000 times less effective in stimulating in vitro and/or in vivo regulatory T cells and shows greater in vivo therapeutic efficacy, wherein the polypeptide is selected from the group consisting of: (i) the polypeptide comprising the sequence of SEQ ID NO 1; (ii) the polypeptide comprising the sequence of SEQ ID NO 2; (iii) the polypeptide comprising the sequence of SEQ ID NO 3; (iv) the polypeptide comprising the sequence of SEQ ID NO 4; (v) the polypeptide comprising the sequence of SEQ ID NO 5; (vi) the polypeptide comprising the sequence of SEQ ID NO 6.

2. The agonist polypeptide of claim 1, wherein said polypeptide comprises the amino acid sequence of SEQ ID NO: 1.

3. The agonist polypeptide of claim 1, wherein said polypeptide comprises the amino acid sequence of SEQ ID NO: 2.

4. The agonist polypeptide of claim 1, wherein said polypeptide comprises the amino acid sequence of SEQ ID NO: 3.

5. The agonist polypeptide of claim 1, wherein said polypeptide comprises the amino acid sequence of SEQ ID NO: 4.

6. The agonist polypeptide of claim 1, wherein said polypeptide comprises the amino acid sequence of SEQ ID NO: 5.

7. The agonist polypeptide of claim 1, wherein said polypeptide comprises the amino acid sequence of SEQ ID NO: 6.

8. A fusion protein comprising the immunomodulatory polypeptide of claim 1, coupled to a carrier protein.

9. The fusion protein of claim 8 wherein the carrier protein is albumin.

10. The fusion protein of claim 8 wherein the carrier protein is the Fc region of a human immunoglobulin.

11. A pharmaceutical composition useful in the treatment of melanoma, comprising as an active ingredient the polypeptide of claim 1 and a pharmaceutically acceptable carrier or diluent.

12. The pharmaceutical composition of claim 11, characterized by comprising as an active ingredient at least two polypeptides described in claim 1.

13. A pharmaceutical composition useful in the treatment of melanoma, which comprises as an active principle the fusion protein described in claim 8.

14. A method of treating in a patient in need of such treatment, comprising administering an effective amount of the polypeptide of claim 1.

15. A method of treating in a patient in need of such treatment, comprising administering an effective amount of the polypeptide of claim 2.

16. A method of treating in a patient in need of such treatment, comprising administering an effective amount of the polypeptide of claim 3.

17. A method of treating in a patient in need of such treatment, comprising administering an effective amount of the polypeptide of claim 4.

18. A method of treating in a patient in need of such treatment, comprising administering an effective amount of the polypeptide of claim 5.

19. A method of treating in a patient in need of such treatment, comprising administering an effective amount of the polypeptide of claim 6.

20. A method of treating in a patient in need of such treatment, comprising administering an effective amount of the polypeptide of claim 7.

21. A method of treating in a patient in need of such treatment, comprising administering an effective amount of the fusion protein of claim 8.

22. A method of treating in a patient in need of such treatment, comprising administering an effective amount of the fusion protein of claim 9.

23. A method of treating in a patient in need of such treatment, comprising administering an effective amount of the fusion protein of claim 10.

24. A method of treating in a patient in need of such treatment, comprising administering an effective amount of the polypeptide of claim 1 in combination with a cancer vaccine.

25. A method of treating in a patient in need of such treatment, comprising administering an effective amount of the polypeptide of claim 2 in combination with a cancer vaccine.

26. A method of treating in a patient in need of such treatment, comprising administering an effective amount of the polypeptide of claim 3 in combination with a cancer vaccine.

27. A method of treating in a patient in need of such treatment, comprising administering an effective amount of the polypeptide of claim 4 in combination with a cancer vaccine.

28. A method of treating in a patient in need of such treatment, comprising administering an effective amount of the polypeptide of claim 5 in combination with a cancer vaccine.

29. A method of treating in a patient in need of such treatment, comprising administering an effective amount of the polypeptide of claim 6 in combination with a cancer vaccine.

30. A method of treating in a patient in need of such treatment, comprising administering an effective amount of the polypeptide of claim 7 in combination with a cancer vaccine.

31. A method of treating in a patient in need of such treatment, comprising administering an effective amount of the fusion protein of claim 8 in combination with a cancer vaccine.

32. A method of treating in a patient in need of such treatment, comprising administering an effective amount of the fusion protein of claim 9 in combination with a cancer vaccine.

33. A method of treating in a patient in need of such treatment, comprising administering an effective amount of the fusion protein of claim 10 in combination with a cancer vaccine.

* * * * *

SEQUENCE LISTING

<160> NUMBER OF SEQ ID NOS: 6

<210> SEQ ID NO 1
<211> LENGTH: 133
<212> TYPE: PRT
<213> ORGANISM: E. coli

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Lys Met Leu Thr Ile Lys Phe Asn Met Pro Lys
        35                  40                  45

Lys Ala Thr Glu Leu Lys His Leu Gln Cys Leu Glu Glu Leu Leu Lys
    50                  55                  60

Pro Leu Glu Val Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 2
<211> LENGTH: 133
<212> TYPE: PRT
<213> ORGANISM: E. coli

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Lys Met Leu Thr Gln Lys Phe Glu Met Pro Lys
        35                  40                  45

Lys Ala Thr Glu Leu Lys His Leu Gln Cys Leu Glu Glu Glu Leu Lys
    50                  55                  60

Pro Leu Glu Val Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 3
<211> LENGTH: 133
<212> TYPE: PRT
<213> ORGANISM: E. coli

<400> SEQUENCE: 3

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

-continued

Asn Pro Lys Leu Thr Ala Met Leu Thr Ile Lys Phe Asn Met Pro Lys
         35                  40                  45

Lys Ala Thr Glu Leu Lys His Leu Gln Cys Leu Glu Glu Leu Leu Lys
 50                  55                  60

Pro Leu Glu Val Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 4
<211> LENGTH: 133
<212> TYPE: PRT
<213> ORGANISM: E. coli

<400> SEQUENCE: 4

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Lys Met Leu Thr Lys Lys Phe Arg Met Pro Lys
         35                  40                  45

Lys Ala Thr Glu Leu Lys His Leu Gln Cys Leu Glu Glu Leu Leu Lys
 50                  55                  60

Pro Leu Glu Val Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 5
<211> LENGTH: 133
<212> TYPE: PRT
<213> ORGANISM: E. coli

<400> SEQUENCE: 5

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Lys Met Leu Thr Ile Lys Phe Glu Met Pro Lys
         35                  40                  45

Lys Ala Thr Glu Leu Lys His Leu Gln Cys Leu Glu Glu Glu Leu Lys
 50                  55                  60

Pro Leu Glu Val Val Leu Asn Leu Ala Gln Ser Lys Asn Phe His Leu
 65                  70                  75                  80

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 6
<211> LENGTH: 133
<212> TYPE: PRT
<213> ORGANISM: E. coli

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Ala Met Leu Thr Ala Lys Phe Ala Met Pro Lys
            35                  40                  45

Lys Ala Thr Glu Leu Lys His Leu Gln Cys Leu Glu Glu Ala Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```